United States Patent
Mangelschots et al.

(10) Patent No.: US 9,908,964 B2
(45) Date of Patent: Mar. 6, 2018

(54) PROCESS FOR PROVIDING ISOCYANURATE MODIFIED METHYLDIPHENYLDIISOCYANATE

(75) Inventors: Nicole Mangelschots, Wilsele (BE); Joris Karel Peter Bosman, Herselt (BE)

(73) Assignee: HUNTSMAN INTERNATIONAL LLC, The Woodlands, TX (US)

(*) Notice: Subject to any disclaimer, the term of this patent is extended or adjusted under 35 U.S.C. 154(b) by 125 days.

(21) Appl. No.: 13/638,636

(22) PCT Filed: Mar. 1, 2011

(86) PCT No.: PCT/EP2011/052999
§ 371 (c)(1),
(2), (4) Date: Oct. 1, 2012

(87) PCT Pub. No.: WO2011/128144
PCT Pub. Date: Oct. 20, 2011

(65) Prior Publication Data
US 2013/0023659 A1 Jan. 24, 2013

(30) Foreign Application Priority Data
Apr. 13, 2010 (EP) .................................. 10159708

(51) Int. Cl.
*C08G 18/79* (2006.01)
*C08G 18/02* (2006.01)
*C07D 251/34* (2006.01)
*C08G 18/76* (2006.01)
*C07D 251/30* (2006.01)

(52) U.S. Cl.
CPC ......... *C08G 18/022* (2013.01); *C07D 251/30* (2013.01); *C07D 251/34* (2013.01); *C08G 18/7671* (2013.01); *C08G 18/791* (2013.01); *C08G 18/794* (2013.01); *C08G 2105/02* (2013.01)

(58) Field of Classification Search
CPC .. C07D 251/34; C08G 18/791; C08G 18/794; C08G 18/7671
USPC ........................................................... 544/193
See application file for complete search history.

(56) References Cited

U.S. PATENT DOCUMENTS

| 4,743,627 | A | 5/1988 | Narayan et al. |
| 5,124,370 | A | 6/1992 | Scholl et al. |
| 2009/0105359 | A1 | 4/2009 | O'Connor et al. |

FOREIGN PATENT DOCUMENTS

| EP | 0 307 742 | 3/1989 |
| EP | 0 472 063 | 2/1992 |
| WO | WO 2009/039332 | 3/2009 |

*Primary Examiner* — Michael L Leonard
(74) *Attorney, Agent, or Firm* — Huntsman International LLC; Robert Diaz

(57) ABSTRACT

A process for providing isocyanurate modified methyl diphenyl diisocyanate is provided,
the process comprises
determine the NCO-value of the MDI;
define the NCO-value for MDI;
define a ratio of the volume of the MDI to be trimerised over volume of the MDI not to be trimerised;
determine, in function of this ratio, the NCO-value of the isocyanurate modified MDI to be provided and the NCO-value of the MDI a target NCO-value for the part of MDI to be trimerised;
divide the MDI in two part according to the defined ratio;
provide a trimerised part of the MDI by trimerising one of these parts until the target NCO-value is obtained; and
terminate the trimerisation by killing the trimerisation catalyst and blend the two parts with each other.

14 Claims, No Drawings

PROCESS FOR PROVIDING ISOCYANURATE MODIFIED METHYLDIPHENYLDIISOCYANATE

CROSS-REFERENCE TO RELATED APPLICATIONS

This application is the National Phase of International Application PCT/EP2011/052999filed Mar. 1, 2011which designated the U.S. and which claims priority to European App. Serial No. 10159708.6filed Apr. 13, 2010. The noted applications are incorporated herein by reference.

The present invention relates to processes for providing isocyanurate modified polymeric methyl diphenyl diisocyanate.

Isocyanurate modified polymeric methyl diphenyl diisocyanate is a variant of polymeric methyl diphenyl diisocyanate (pMDI), which comprises trimerised diisocyanate components.

A process for providing such isocyanurate modified polymeric methyl diphenyl diisocyanate is disclosed in WO2009/039332A1. The isocyanurate modified polymeric methyl diphenyl diisocyanate on industrial scale includes separating a batch of pMDI in two parts. One part is subjected to a trimerising reaction using a catalyst. After trimerising this part of the pMDI batch, the catalyst is killed and the remainder of the original pMDI batch is blended with the trimerised part, thereby providing the isocyanurate modified polymeric methyl diphenyl diisocyanate. The properties, e.g. the NCO-value or the viscosity of the isocyanurate modified polymeric methyl diphenyl diisocyanate is checked and if not matching the aimed value, an adjustment of the properties is made by either again trimerising or by further adding untrimerised pMDI. This process is labor intensive and requires consecutive sampling and measuring steps to arrive at the desired isocyanurate modified polymeric methyl diphenyl diisocyanate.

It is an object of the present invention to provide isocyanurate modified polymeric methyl diphenyl diisocyanate, and a process for providing such isocyanurate modified polymeric methyl diphenyl diisocyanate, which is less labor intensive and avoids partially or completely the necessity to use consecutive sampling and measuring steps, and optionally correcting additions of components to provide the end product its target product properties.

According to a first aspect of the present invention, a process for providing isocyanurate modified methyl diphenyl diisocyanate is provided. The process comprises
  providing methyl diphenyl diisocyanate (MDI);
  determine the NCO-value of the MDI (NCOstart);
  define the NCO-value for the isocyanurate modified methyl diphenyl diisocyanate to be provided (NCOend);
  define a ratio of the volume of the MDI to be trimerised over volume of the MDI not to be trimerised;
  determine, in function of the ratio, the NCO-value of the isocyanurate modified methyl diphenyl diisocyanate to be provided and the NCO-value of said MDI a target NCO-value (NCOtarget) for the part of MDI to be trimerised, said the target NCO-value to be obtained during trimerisation;
  divide the MDI in a first part (Vt) being the part of MDI to be trimerised and a second part (Vo) according to the ratio;
  provide a trimerised part of the MDI by trimerising the first part (Vt) using a trimerisation catalyst until the target NCO-value is obtained;
  terminate the trimerisation by killing the trimerisation catalyst and blend the trimerised part and the second part, thereby providing the isocyanurate modified methyl diphenyl diisocyanate.

According to some embodiments, determining the target NCO-value (NCOtarget) for the part of MDI to be trimerised may be based on the ratio and the difference between the NCO-value of the MDI (NCOstart) and the NCO-value for the isocyanurate modified methyl diphenyl diisocyanate to be provided (NCOend).

This difference between the NCO-value of the MDI (NCOstart) and the NCO-value for the isocyanurate modified methyl diphenyl diisocyanate to be provided (NCOend) is hereinafter also referred to as delta NCO, wherein delta NCO=NCOstart−NCOend According to some embodiments, the MDI may be polymeric MDI (pMDI).

Polymeric methyl diphenyl diisocyanate (pMDI) is to be understood as compositions of one or more methyl diphenyl diisocyanate isomers (4,4' MDI, 2,4'MDI or 2,2'MDI) with species comprising more than two phenylisocyanate groups. These species comprising more than two phenylisocyanate groups are also referred to as oligomers of methyl diphenyl diisocyanate.

Suitable pMDI may be the so called crude pMDI, i.e. the mixture of polymeric methyl diphenyl diisocyanate obtained by reacting the corresponding mixture of methyl diphenyl diamine isomers and oligomers with phosgene.

Alternatively, pMDI obtained by removal of at least part of the methyl diphenyl diisocyanate isomers from the crude pMDI may be used.

Suitable pMDI may comprise typically between 25% w and 75% w of methyl diphenyl diisocyanate isomers, e.g. between 25% w and 70% w, preferably between 28% w and 65% w, more preferred between 30% w and 60% w such as typically 45% w, 39% w or 33% w (all % w expressed as weight of the component(s) over total weight of product in which the component(s) is (are) present).

Alternatively, pure MDI may be used, i.e. MDI comprising more than 75% w methyl diphenyl diisocyanate isomers, i.e. 4,4'MDI, 2,4'MDI and/or 2,2'MDI.

The use of pMDI is preferred.

The MDI, preferably pMDI, used as starting product may have an NCO-value in the range of 28 to 33.6.

The acidity of the MDI, typically pMDI, used as starting product may be less than 300 ppm, typically between 10 and 200 ppm. This acidity of the MDI, typically pMDI, used as starting product is hereinafter referred to as "Astart". Acidity is to be understood as the amount of HCl released from the isocyanate through urethane formation with n-propanol and titrated with alcoholic KOH (ASTM D5629).

The viscosity is of the pMDI may be in the range of 50 to 500 cP, preferably in the range of 100 to 450 cP, such as in the range of 125 to 300 cP. Viscosity is to be understood as the viscosity at 25 deg C., measured using a Brookfield cone/plate viscometer at a working temperature of 25° C.

After trimerising the first part of the MDI, being preferably pMDI, the trimerisation is to be stopped as soon as possible when this first part reaches its target NCO-value. Preferably the trimerisation is stopped by killing at least part of the catalyst with the acid present in the remainder of the MDI, i.e. the second part Vo. In some circumstances, the blending of the trimerised part and the second part (Vo) may be sufficient to terminate the trimerisation.

Optionally a catalyst killing agent is used to terminate the trimerisation before or during the blending of the trimerised part and the second part (Vo). Alternatively the acid of the second part (Vo) and an additional catalyst killing agent is used to terminate the trimerisation.

Suitable catalyst killing agents are thionylchloride and sulfonylchlorides such as toluenesulfonylchloride and methanesulfonylchloride, aliphatic and aromatic acid chlorides such as acetylchloride and benzoylchloride, organic and inorganic acids such as acetic acid, oxalic acid, methanesulfonic acid, trifluoromethanesulfonic acid, hydrochloric acid, sulfuric acid, phosphoric acid and mixtures thereof. Alkylating agents such as methylchloride, dimethylsulfate, sulfonates such as para toluene sulfonic acid methylester, phosphates such as diethylphosphate and compounds bearing labile chloride or bromide bonds such as PCl5, POCl3 and the like. Most preferred ones are thionylchloride, benzoylchloride and acetylchloride.

Preferably, the acid present in the second part (Vo) may be sufficient, hence is used to terminate the trimerisation reaction, without an additional catalyst killing agent. The choice of the part of the pMDI to be trimerised and the target NCO-value may be influenced by the acidity of the pMDI. In some circumstances, the part and the NCO-target value may be chosen such that the catalyst necessary to reach the target NCO-value, and hence the amount of acid to kill the catalyst, match with the acid present in the second part of the pMDI.

According to some embodiments, the trimerisation may be stopped by killing the catalyst with components present in the second part (Vo).

The advantage of the process according to the invention is that the end product is provided in a controlled way with a preset NCO-value, without the need of checking and adjusting by additional blending operations. The obtained isocyanurate modified MDI, preferably pMDI, hence may be provided using only one blending step, and the NCO-value of this isocyanurate modified MDI is not necessarily to be adjusted by adding additional untrimerised MDI during following blending steps.

The NCO-value of MDI, preferably pMDI, prior to, during or after trimerisation, can be determined by measuring the refractive index of the MDI.

It was found that the refractive index, measured at a given temperature, typically at 25 deg C., is linearly correlated to the NCO-value of the product measured.

The ri, measured at a given temperature, typically at 25 deg C., is linearly correlated to the NCO-value of the product measured, and this according to a formula:

$$\text{"NCO"}=a*\text{"}ri\text{"}+b$$

The terms a and b may vary in function of the equipment used and should be determined using standard reference samples.

The refractive index (also referred to as ri) is measured using an Abbe refractometer at 25° C.

As such, using a known correlation, the end point of the trimerisation of the first part of the pMDI, i.e. when the pMDI subjected to trimerisation reaches the target NCO-value, can be monitored by determining the ri of the pMDI during trimerisation. The ri can be measured off-line or in-line, this both in case of batch process or a continuous process.

During trimerisation of pMDI, the viscosity raises in function of the provision of trimers. The more trimers are provided, i.e. the further the trimerisation process proceeds, the higher the viscosity becomes. This has also as a consequence that the more NCO-groups are consumed in the trimerisation process, hence the lower the NCO-value becomes, the higher the viscosity will be.

According to some embodiments, the ratio (X) and the target NCO-value may meet the formula $$NCOtarget=(X+1)*NCOend-X*NCOstart.$$

In other words, NCOtarget=NCOend−X*(delta NCO)

According to some embodiments, the amount of trimerisation catalyst (Vc) may be determined in function of the target NCO-value.

The catalysts used typically have a number of nitrogens in its molecular structure, which nitrogens are responsible for the catalytic activity. The number of nitrogens in the molecular structure of the catalyst is hereinafter referred to as "#N".

This amount of trimerisation catalyst (Vc) may be determined based upon the type of catalyst used, the NCO value of the starting product (NCOstart), the NCO value of the MDI after trimerisation (NCOtarget), and the acidity of the MDI, typically pMDI used as starting product (Astart). The amount of trimerisation catalyst Vc may be determined by using the formula $$Vc=Astart*[\text{molar weight catalyst}/(\#N*36.46)]+F1*(NCOstart-NCOtarget)$$

36.46 is the molar weight of HCl.

F1 is an empirically defined factor, which is influenced by the scale of the batch in production, the speed of trimerisation and the catalyst used.

Optionally a catalyst killing agent may be used to terminate the trimerisation before or during the blending of the trimerised part and the second part (Vo).

The use of a catalyst killer was considered not necessary to obtain a stable MDI (typically pMDI) in case the amount of catalyst (Vc) met the comparison:

$$Vc \leq Astart*(1+X)*[\text{molar weight catalyst}/(\#N*36.46)]$$

or, in case Vc was calculated, defining F1 in such a manner that the trimerisation step takes more than 10 minutes and in case the blend ratio is more than 1.5.

Additional advantage is the reduced acidity of the end product. 36.46 is the molar weight of HCl.

According to some embodiments, the target NCO value may be more than 17.

Optionally the target NCO value is more than 18, even more than 19 or more than 20.

In case the target NCO value is set lower than this limit, the viscosity of the MDI, typically pMDI, during trimerising becomes too high, which might cause damage to the process installation, such as e.g. the mixing equipment or the pumps used.

According to some embodiments, during trimerising, the temperature of the trimerising MDI may be kept within a range of 20 to 150 deg C.

More preferred, the temperature is kept in the range of 40 to 120 deg C.

The trimerising reaction is exothermic. By carefully defining the amount of pMDI to be trimerised, i.e. the first part, and the amount of catalyst to be used, as well as the end point of the trimerisation (i.e. NCO-value to be aimed at), the temperature will be kept within the range as set out above. Optionally however, cooling means may be used to evacuate thermal energy from the reactor in which the trimerising reaction takes place.

According to some embodiments, the ratio of first part and second part may be in the range of 0.5 to 20.

More preferred, the ratio of first part and second part ranges from 1 to 16, e.g. 15.

The viscosity of the isocyanurate modified methyl diphenyl diisocyanate (MDI) as a result of the processes according to the present invention, may range from 150 cP to 3000 cP, more preferred between 200 cP and 1000 cP, e.g. 400 cP or 700 cP.

The acidity of the isocyanurate modified methyl diphenyl diisocyanate (MDI) preferably ranges from 0 to 300 ppm, more preferred between 0 and 200 ppm.

According to some embodiments, the process may be a discontinuous or batch process, or may be a continuous process.

It is understood that the process according to the present invention can be executed batch-wise or continuously.

When applying the process batch wise, the actual quantity of pMDI to be treated and modified during one batch is a given volume Vstart of pMDI. The batch is split into two parts, in this case being two volumes. The first part represents a first volume to be trimerised, prior to blending it back to the second part Vo, being the remaining volume. The parts or volumes Vt and Vo have typically a ratio of 0.5 to 20, more preferred, the ratio of volumes Vt and Vo ranges from 1 to 16, e.g. 15.

When applying the process in a continuous way, the MDI, typically pMDI, is provided as a continuous stream, expressed as a volume per time unit. The first part Vt to be trimerised is a first fraction of this stream. The second part Vo is the remainder of the stream of MDI after taking out the first part Vt. The first part Vt represents the actual quantity of MDI to be treated and modified per time unit. The MDI stream per time unit is split into two streams, i.e. the volume Vt of the first stream per time unit (the one to be trimerised according to the present invention) and the volume Vo of the second stream per time unit (the one not to be trimerised according to the present invention). After trimerising the first part Vt, the two parts, being two streams of MDI (one of them being trimerised), are blended with each other at the same ratio.

It is understood that the throughput time of the first and second part through the continuous process might not be identical. This throughput time is the time it takes for an infinite fraction of MDI to flow from the point where the two parts Vt and Vo are separated, until the point where the part Vo and the part Vt, after trimerising, are combined again.

However it was noticed that the NCO-value of the MDI (NCOstart) varies that slow, that the deviation of the defined NCO-value of the isocyanurate modified methyl diphenyl diisocyanate (NCOend) with the actually obtained NCO-value of the isocyanurate modified methyl diphenyl diisocyanate is within the product tolerances.

A difference of throughput time of 5 to 60 minutes can be accepted.

In case of a batch process, the trimerisation step may take less than 2 hours, and at least 5 minutes, but is typically preformed in a time period of 8 minutes to 15 minutes, though time periods in the range 10 minutes to 90 minutes may be used.

The isocyanurate modified methyl diphenyl diisocyanate, typically isocyanurate modified polymeric methyl diphenyl diisocyanate, being the product resulting from a process according to the present invention, may have an NCO value in the range of 28 to 33.5. The NCO value means the weight of the NCO-groups in a volume of isocyanate over the total weight of the volume of isocyanate.

The independent and dependent claims set out particular and preferred features of the invention. Features from the dependent claims may be combined with features of the independent or other dependent claims as appropriate.

The above and other characteristics, features and advantages of the present invention will become apparent from the following detailed description, which illustrate, by way of example, the principles of the invention. This description is given for the sake of example only, without limiting the scope of the invention.

The present invention will be described with respect to particular embodiments.

It is to be noticed that the term "comprising", used in the claims, should not be interpreted as being restricted to the means listed thereafter; it does not exclude other elements or steps. It is thus to be interpreted as specifying the presence of the stated features, steps or components as referred to, but does not preclude the presence or addition of one or more other features, steps or components, or groups thereof. Thus, the scope of the expression "a device comprising means A and B" should not be limited to devices consisting only of components A and B. It means that with respect to the present invention, the only relevant components of the device are A and B.

Throughout this specification, reference to "one embodiment" or "an embodiment" are made. Such references indicate that a particular feature, described in relation to the embodiment is included in at least one embodiment of the present invention. Thus, appearances of the phrases "in one embodiment" or "in an embodiment" in various places throughout this specification are not necessarily all referring to the same embodiment, though they could. Furthermore, the particular features or characteristics may be combined in any suitable manner in one or more embodiments, as would be apparent to one of ordinary skill in the art.

EXAMPLE 1 (700 cP End Product)

A polymeric MDI with properties Acidity: 110 ppm, NCO: 30.2%, is provided.

The end product to be provided is an isocyanurate modified methyl diphenyl diisocyanate with an NCO-value 29.1% (NCOend).

The blend ratio of the volume of the MDI to be trimerised over volume of the MDI not to be trimerised is defined to be ½

The difference in NCO value to be obtained is delta NCO=NCOstart−NCOend, or 1.1%

The target NCO-value (NCOtarget) to be obtained during trimerisation for the part of MDI to be trimerised is (X+1)*NCOend−X*NCOstart, or 26.9%.

The pMDI was divided in a first part (Vt) to be trimerised and a second part (Vo) not to be trimerised.

An amount of 716 ppm catalyst name Jeffcat TR 90, being a trimerisation catalyst with 6 nitrogen was calculated using the formula $$Vc = A\text{start} * [\text{molar weight catalyst}/(\#N * \text{molar weight HCl})] + F1 * (\text{NCOstart} - \text{NCOtarget})$$

wherein
Astart is 170 ppm
molar weight catalyst is 342
N is 6
F1 was empirically defined by means of several reference experiments and found to be 165
Using this formula, Vc is 716 ppm
In the experiment, Vc of 692 ppm was used.

A trimerised part of the MDI was provided by trimerising the first part (Vt) at a temperature of 50° C. and atmospheric pressure during 33 minutes, until the target NCO-value is obtained.

The second part was added to the trimerised part, thereby killing the catalyst and providing the isocyanurate modified methyl diphenyl diisocyanate having an NCO value of 29.1 and an acidity of 60 ppm.

EXAMPLE 2 (2000 cP End Product)

A polymeric MDI with properties Acidity: 170 ppm, NCO: 30.3%, is provided.

The end product to be provided is an isocyanurate modified methyl diphenyl diisocyanate with an NCO-value 28.6% (NCOend).

The blend ratio of the volume of the MDI to be trimerised over volume of the MDI not to be trimerised is defined to be 1/1.5

The difference in NCO value to be obtained is delta NCO=NCOstart−NCOend, or 1.7%

The target NCO-value (NCOtarget) to be obtained during trimerisation for the part of MDI to be trimerised is (X+1)*NCOend−X*NCOstart, or 26.0%.

The pMDI was divided in a first part (Vt) to be trimerised and a second part (Vo) not to be trimerised.

An amount of 979 ppm catalyst Jeffcat TR 90, being a trimerisation catalyst with 6 nitrogen was calculated using the formula $$Vc = A\text{start} * [\text{molar weight catalyst}/(\#N * \text{molar weight HCl})] + F1 * (NCO\text{start} - NCO\text{target})$$

wherein
Astart is 170 ppm
molar weight catalyst is 342
N is 6
F1 was empirically defined by means of several reference experiments and found to be 165
Using this formula, Vc is 979 ppm
In the experiment, Vc of 893 ppm was used.

A trimerised part of the MDI was provided by trimerising the first part (Vt) at a temperature of 50° C. and atmospheric pressure during 60 minutes, until the target NCO-value is obtained.

The second part was added to the trimerised part, thereby killing the catalyst and providing the isocyanurate modified methyl diphenyl diisocyanate having an NCO value of 28.6 and an acidity of 70 ppm.

It is to be understood that although preferred embodiments and/or materials have been discussed for providing embodiments according to the present invention, various modifications or changes may be made without departing from the scope and spirit of this invention.

The invention claimed is:

1. A process for producing isocyanurate modified methyl diphenyl diisocyanate, the process comprising:
providing an amount of a methyl diphenyl diisocyanate (MDI) and determining an NCO-value of the MDI (NCOstart);
defining an NCO-value for the isocyanurate modified methyl diphenyl diisocyanate to be produced (NCOend);
defining a ratio (X) of a volume of MDI to be trimerised over a volume of MDI not to be trimerised;
determining a target NCO-value (NCOtarget) for the volume of MDI to be trimerised, wherein (i) NCOtarget has a lower value than NCOend and (ii) NCOtarget is determined using the following equation:

$$NCO\text{target} = (X+1) * NCO\text{end} - X * NCO\text{start}$$

dividing said amount of MDI into a first volume (Vt) to be trimerised and a second volume (Vo) to not be trimerised according to said ratio (X);
trimerising the first volume using a trimerisation catalyst (Vc) thereby forming a trimerised volume, wherein the amount of trimerisation catalyst is determined by the following equation:

$$Vc \leq A\text{start} * (1+X) * [\text{molar weight catalyst}/(\#N * 36.46)]$$

wherein Astart is the acidity of said MDI, and wherein the NCO-value of the first volume (Vt) is monitored during trimerisation by measuring the refractive index of the MDI in the first volume (Vt); and
terminating trimerisation of the first volume (Vt) after the target NCO-value is obtained by blending the second volume (Vo) to the first volume (Vt) thereby forming an isocyanurate modified methyl diphenyl diisocyanate having an NCO value of as NCOend in a single blending operation.

2. The process of claim 1, wherein the amount of trimerisation catalyst (Vc) used in trimerising the first volume (Vt) is calculated using the following equation:

$$Vc = A\text{start} * [\text{molar weight catalyst}/(\#N * 36.46)] + F1 * (NCO\text{start} - NCO\text{target})$$

wherein Astart is the acidity of said MDI and F1 is an empirically defined factor.

3. The process of claim 1, wherein terminating the trimerisation comprises killing the catalyst only with components present in the second volume (Vo).

4. The process of claim 1, wherein the target NCO-value is more than 17.

5. The process of claim 1, wherein during trimerising, the temperature for trimerising the first volume (Vt) of MDI is kept within a range of 20 to 150deg C.

6. The process of claim 1, wherein the ratio of the first volume (Vt) and the second volume (Vo) is in a range of 0.5 to 20.

7. The process of claim 1, wherein said process is a continuous process.

8. The process of claim 1, wherein said process is a batch process.

9. A process for forming isocyanurate modified methyl diphenyl diisocyanate, comprising:
providing a methyl diphenyl diisocyanate and determining an NCO-value of the methyl diphenyl diisocyanate (NCOstart);
defining an NCO-value for the isocyanurate modified methyl diphenyl diisocyanate to be formed (NCOend);
defining a ratio (X) of a first volume of methyl diphenyl diisocyanate to be trimerised over a second volume of methyl diphenyl diisocyanate not to be trimerised;
determining a target NCO-value (NCOtarget) for the first volume of methyl diphenyl diisocyanate to be trimerised, wherein (i) NCOtarget has a lower value than NCOend and (ii) NCOtarget is determined using the following equation:

$$NCO\text{target} = (X+1) * NCO\text{end} - X * NCO\text{start};$$

dividing the methyl diphenyl diisocyanate into a first volume (Vt) to be trimerised and a second volume (Vo) to not be trimerised according to said ratio (X)

trimerising the first volume of methyl diphenyl diisocyanate using a trimerisation catalyst, wherein the amount of trimerisation catalyst (Vc) is determined by the following equation:

$$Vc \leq A\text{start} * (1+X) * [\text{molar weight catalyst}/(\#N * 36.46)]$$

wherein Astart is the acidity of said methyl phenyl diisocyanate, and wherein the NCO-value of the first volume (Vt) is monitored during trimerisation by measuring the refractive index of the methyl diphenyl diisocyanate in the first volume (Vt); and terminating trimerisation of the first volume (Vt) after the target NCO-value is obtained by blending the second volume (Vo) to the first volume (Vt) thereby forming an isocyanurate modified methyl diphenyl diisocyanate having the same NCO value as NCOend in a single blending operation.

10. The process of claim 9, wherein methyl diphenyl diisocyanate is polymeric methyl diphenyl diisocyanate.

11. The process of claim 9, wherein the ratio is a volumetric ratio and is between 0.5 and 20.

12. A process for forming isocyanurate modified polymeric methyl diphenyl diisocyanate, comprising:

providing a polymeric methyl diphenyl diisocyanate and determining an NCO-value of the polymeric methyl diphenyl diisocyanate (NCOstart);

defining an NCO-value for the isocyanurate modified polymeric methyl diphenyl diisocyanate to be formed (NCOend);

defining a ratio (X) of a first volume of polymeric methyl diphenyl diisocyanate to be trimerised over a second volume of polymeric methyl diphenyl diisocyanate not to be trimerised;

determining a target NCO-value (NCOtarget) for the first volume of polymeric methyl diphenyl diisocyanate to be trimerised, wherein (i) NCOtarget has a lower value than NCOend and (ii) NCOtarget is determined using the following equation:

$$\text{NCOtarget} = (X+1) \cdot \text{NCOend} - X \cdot \text{NCOstart};$$

dividing said amount of polymeric methyl diphenyl diisocyanate into a first volume (Vt) to be trimerised and a second volume (Vo) to not be trimerised according to said ratio (X);

trimerising the first volume (Vt) using a trimerisation catalyst, wherein the amount of trimerisation catalyst (Vc) is determined by the following equation:

$$Vc < A\text{start} \cdot (1+X) \cdot [\text{molar weight catalyst}/(\#N \cdot 36.46)]$$

wherein Astart is the acidity of said polymeric methyl diphenyl diisocyanate, and wherein the NCO-value of the first volume (Vt) is monitored during trimerisation by measuring the refractive index of the polymeric methyl diphenyl diisocyanate in the first volume (Vt); and terminating trimerisation of the first volume (Vt) after the target NCO-value is obtained by blending the second volume (Vo) to the first volume (Vt) thereby forming an isocyanurate modified polymeric methyl diphenyl diisocyanate having the same NCO value integer or fractional number as NCOend by a single blending operation.

13. The process of claim 12, wherein the step of forming the isocyanurate modified polymeric methyl diphenyl diisocyanate comprises combining the trimerised first volume of polymeric methyl diphenyl diisocyanate and the second volume of polymeric methyl diphenyl diisocyanate.

14. The process of claim 12, wherein the ratio is a volumetric ratio and is between 0.5 and 20.

* * * * *